United States Patent [19]

Whitehead et al.

[11] Patent Number: 4,699,646

[45] Date of Patent: Oct. 13, 1987

[54] DINITROANILINE YIELD ENHANCING AGENTS FOR LEGUMES

[75] Inventors: David L. Whitehead, Trenton; Prithvi R. Bhalla, Hightstown, both of N.J.

[73] Assignee: American Cyanamid Co., Stamford, Conn.

[21] Appl. No.: 798,704

[22] Filed: Nov. 15, 1985

Related U.S. Application Data

[63] Continuation of Ser. No. 602,631, Apr. 24, 1984, abandoned, which is a continuation of Ser. No. 362,366, Mar. 26, 1982, abandoned, which is a continuation-in-part of Ser. No. 272,628, Jun. 11, 1981, abandoned.

[51] Int. Cl.$^4$ ............................................. A01N 33/02
[52] U.S. Cl. ........................................... 71/77; 71/76; 71/103; 71/105; 71/121
[58] Field of Search .................... 71/77, 76, 121, 125, 71/103, 105, 126, 27, 7

[56] References Cited

U.S. PATENT DOCUMENTS

| | | |
|---|---|---|
| 3,697,253 | 10/1972 | MacMurray ...................... 71/121 X |
| 4,025,538 | 5/1977 | Lutz et al. ......................... 260/397.6 |
| 4,073,638 | 2/1978 | MacMurray ...................... 71/121 X |
| 4,087,460 | 5/1978 | Porter et al. ..................... 71/121 X |
| 4,101,582 | 7/1978 | Lutz et al. ........................ 71/121 X |
| 4,123,250 | 10/1978 | Kupelian ................................ 71/76 |
| 4,124,639 | 11/1978 | Lutz et al. ........................ 71/121 X |
| 4,136,117 | 1/1979 | Diehl et al. ...................... 71/121 X |

FOREIGN PATENT DOCUMENTS 2361463 6/1974 Fed. Rep. of Germany ........ 71/121

OTHER PUBLICATIONS

Condensed Chemical Dictionary, 6th Ed., 1961, Reinhold Pub. Corp., N.Y., p. 567.

*Primary Examiner*—Kenneth M. Schor
*Attorney, Agent, or Firm*—H. G. Jackson

[57] ABSTRACT

The invention relates to a method to increase the yield of stem, root and of leguminous crops by applying a yield enhancing amount of a dinitroaniline compound to the leaves and stems of said plants or to soil containing the seeds thereof.

7 Claims, No Drawings

DINITROANILINE YIELD ENHANCING AGENTS FOR LEGUMES

The application is a continuation of copending Ser. No. 602,631 filed Apr. 24, 1984 (now abandoned) which is a continuation of abandoned Ser. No. 362,366 filed Mar. 26, 1982 which is a continuation-in-part of abandoned Ser. No. 272,628 filed June 11, 1981.

SUMMARY OF THE INVENTION

The invention is a method to improve the yield of stem and root crops and of the seeds and of the fruits of leguminous plants by applying to the foliage and stems of said plants, or to soil containing the seeds of said plants a yield enhancing amount of a compound of formula (I)

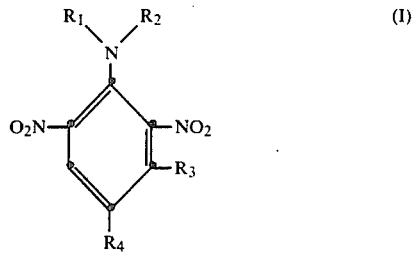

wherein $R_1$ is selected from H, $CH_3$, and $C_2H_5$; $R_2$ is selected from H, $C_1$-$C_5$ alkyl saturated or unsaturated straight chain or branched, and optionally substituted with OH, Cl, and $OCH_3$; $R_3$ is selected from $OCH_3$, or $CH_2R_5$; $R_4$ is selected from $CH_3$, $C_2H_5$, n-$C_3H_7$, i-$C_3H_7$, n-$C_4H_9$, $SO_2CH_3$, $SO_2NH_2$, and $CF_3$; $R_5$ is selected from H, $OCH_3$, and CN.

A preferred group of compounds represented by formula (I) above are those wherein $R_1$ is H, or $C_2H_5$; $R_2$ is H, or $C_3$-$C_5$ branched chain alkyl, optionally substituted with OH, Cl, and $OCH_3$; $R_3$ is $CH_3$, $CH_2OCH_3$; and $CH_2CN$; $R_4$ is $CH_3$, $C_2H_5$, n-$C_3H_7$, and i-$C_3H_7$.

Another, more preferred group of compounds of formula (I) are those, wherein $R_1$ is H; $R_2$ is $CH(CH_3)_2$, $CH(CH_3)C_2H_5$, $CH(C_2H_5)_2$, and

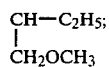

$R_3$ is $CH_3$, or $CH_2OCH_3$; $R_4$ is $C_2H_5$, n-$C_3H_7$, or i-$C_3H_7$.

Of specific interest is the compound: N-isopropyl-2,6-dinitro-4-propyl-m-toluidine.

The compounds of formula (I) are disclosed in U.S. Pat. Nos. 4,025,538; No. 4,101,582, and No. 4,288,385; all of the above are incorporated herein by way of reference.

As indicated above, application of a compound of formula (I) to stem, root and to leguminous crops or to soil in which the seeds of such crops are sown increases the yields of same.

Obviously, yield increases of stem crops, such as sugarcane, potatoes, cassava root, sweet potatoes, taro root, garlic and onions; root crops, such as sugarbeets, carrots, horseradish, radishes, turnips and yams, and leguminous crops, are most advantageous to the farmer. The real significance of the invention, however, lies in the fact that leguminous crops are a good and cheap source of high quality protein, suitable to replace at least in part meat proteins which are essential to prevent malnutrition, yet are in short supply worldwide.

An additional advantage of using the compounds of formula (I) may manifest itself in increased branching, earlier and more uniform flowering, and earlier and more uniform maturing of said leguminous plants.

In practice, we have found, that the application of a compound of formula (I) to the foliage of seedling plants or to soil containing the seeds of said plants in amounts of from about 0.1 kg per hectare to about 1.5 kg per hectare and preferably from about 0.2 to about 1.0 kg per hectare is sufficient to achieve the desirable and advantageous biological responses described above.

The compounds of formula (I) are formulated as dusts, dust concentrates, wettable powders, granulars, emulsion concentrates, and the like.

Dusts are generally prepared by grinding together from about 1% to 15% by weight of the active material with from about 99% to 85% by weight of a solid diluent, such as attaclay, kaolin, diatomaceous earth, fullers earth, talc, pumice or the like.

Dust concentrates are prepared in similar fashion to the dusts excepting that generally about 15% to about 95% by weight of active material is used.

Granular formulations may be prepared by applying a liquid solution of the active material to sorptive granular carriers such as attaclay, kaolin or diatomite granules. Alternatively, they may be mixed with inert carriers and applied to non-sorptive granules, such as sand or limestone.

Wettable powders are prepared by grinding the active ingredient with a solid carrier, such as used in the dust formulations. Usually, about 25% to 75% by weight of the active material and from about 73% to 23% by weight of solid carrier is used. In addition, there is generally added about 1% to 5% by weight of a dispersing agent, such as alkali metal salts of naphthalene sulfuric acid and anionic-nonionic blends, and from about 1% to 5% by weight of a surfactant, such as polyoxyethylene alcohols, acids, adducts, sorbitan fatty acid esters and sorbitol esters.

Emulsion concentrates are prepared by dissolving 15% to 70% by weight of the compound in 85% to 30% by weight of a solvent such as benzene, toluene, xylene, kerosene, 2-methoxy ethanol, propylene glycol, diethylene glycol, diethylene glycol monomethyl ester, formamide, methylformamide and the like, and mixtures thereof. Advantageously, surfactants such as polyoxyethylated vegetable oil or an alkyl phenoxy polyoxyethylene ethanol are also incorporated in amounts of 1% to 5% by weight of said concentrate.

In using wettable powders, emulsion concentrates and the like, the formulated material is generally dispersed in water and applied at a rate of from 0.1 kg hectare to about 1.0 kg per hectare to the plants or to the soil containing the seeds of said plants.

The invention is further illustrated by the following examples which are not to be taken as being limitative thereof.

EXAMPLE 1

Evaluation of test compounds for increasing the dry weight of soybean pods

In the following tests, the appropriate compounds are dissolved or dispersed in acetone:water (50:50) mixtures at the final concentration corresponding to the kg/ha rates indicated in Table I below. The solutions also contain 0.1% to 0.25% v/v colloidal BIOFILM ® (a product of Colloidal Products Corp.) which is a mixture of alkyl aryl polyethoxyethanol, free and combined fatty acids, glycol ethers, dialkylbenzene carboxylate and 2-propanol.

In these tests, the soybean (*Glycine max.* var. Adelphia) seedlings are at the first and fifth trifoliate stage, respectively, when treated (one plant per 17.8 cm pot).

The pots are watered, treated and placed on benches in a random arrangement in the greenhouse. Normal watering and fertilizing practices are followed (pesticides are applied to the plants as needed). Minimum day and night temperature of 18° C. is maintained during cooler periods of the year. Normal daily fluctuations occur during the summer season.

Plants are sprayed to provide the kg/ha rates indicated in Table I below. Each treatment is replicated five to nine times.

At, or near maturity the pods are harvested and dried. The yields are averaged and compared to those obtained from the untreated controls, and are expressed as % increase over the controls.

TABLE I

Evaluation of the effect of compounds of the invention on soybeans
$R_1$ is H in this tabulation, unless shown otherwise

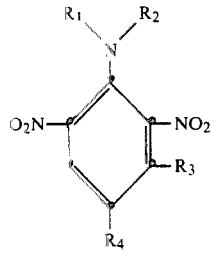

| | | | | % Increase in pod dry wt over control | | | | | |
|---|---|---|---|---|---|---|---|---|---|
| | | | | 1st Trifoliate kg/ha | | | 5th Trifoliate kg/ha | | |
| No. | $R_2$ | $R_3$ | $R_4$ | 0.2 | 0.4 | 0.6 | 0.2 | 0.4 | 0.6 |
| 1 | —CH(CH$_3$)$_2$ | —CH$_2$OCH$_3$ | —C$_2$H$_5$ | 20.6 | — | 7.2 | 25.3 | 19.6 | 17.5 |
| 2 | —CH(CH$_3$)$_2$ | —CH$_3$ | —CH(CH$_3$)$_2$ | 2.1 | 6.3 | 6.4 | 21.5 | 20.8 | 22.3 |
| 3 | —CH(CH$_3$)C$_2$H$_5$ | —CH$_2$OCH$_3$ | —C$_3$H$_7$—n | 6.6 | 11.0 | 8.0 | 24.2 | 23.9 | 34.0 |
| 4 | —CH(C$_2$H$_5$)$_2$ | —CH$_3$ | —C$_3$H$_7$—n | 17.7 | 22.7 | 18.0 | 28.3 | 22.0 | 18.3 |
| 5 | —CH(CH$_3$)$_2$ | —CH$_2$OCH$_3$ | —C$_3$H$_7$—n | 17.5 | 40.3 | 17.0 | 31.45 | 18.45 | 28.4 |
| 6 | H | —CH$_3$ | —C$_3$H$_7$—n | 28.5 | 17.5 | 20.0 | 27.6 | 44.6 | 37.6 |
| 7 | —CH(CH$_3$)$_2$ | —CH$_3$ | —C$_3$H$_7$—n | 26.6 | 21.4 | 25.4 | 34.1 | 27.4 | 24.0 |
| 8 | —CH(CH$_2$OCH$_3$)—C$_2$H$_5$ | —CH$_3$ | —C$_3$H$_7$—n | 29.8 | 26.0 | 13.0 | 52.8 | 42.2 | 58.8 |
| 9 | —CH(CH$_3$)$_2$ | —CH$_3$ | —C$_4$H$_9$—n | 16.4 | 42.2 | 31.2 | 35.9 | 26.9 | 11.1 |
| 10 | —C$_3$H$_7$—n | —CH$_3$ | —C$_3$H$_7$—n | 5.1 | 2.0 | 5.0 | 17.7 | 22.0 | 14.3 |
| 11 | —CH(CH$_3$)$_2$ | —CH$_2$—CN | —C$_3$H$_7$—n | — | 8.3 | 3.2 | 32.5 | 24.6 | 44.5 |
| 12 | —CH(CH$_3$)—CH$_2$CH$_2$OH | —CH$_3$ | —C$_3$H$_7$—n | 3.5 | 10.2 | — | 16.2 | 17.7 | 12.5 |
| 13 | —CH(CH$_3$)—CH$_2$CH$_2$—Cl | —CH$_3$ | —C$_3$H$_7$—n | — | 11.4 | 11.4 | 7.4 | 11.6 | 14.4 |
| 14 | $R_1$ = C$_2$H$_5$, $R_2$ = CH(CH$_3$)$_2$ | —CH$_3$ | —C$_3$H$_7$—n | 5.5 | 5.2 | 3.1 | 24.8 | 38.3 | 29.6 |

EXAMPLE 2

Evaluation of a compound of the invention for increasing the pod yields of soybeans, applied preemergent as a granular formulation Procedure A conventional granular formulation containing 0.1% by weight of N-isopropyl-2,6-dinitro-4-propyl-m-toluidine is broadcast into the seed furrow at the time of planting, and at the rates shown in Table IIa below. The soybean (*Glycine max.* var. Adelphia) seeds are planted in 16.5 cm (dia) pots. Each test is replicated 10 times.

The pots are watered and placed on benches in a random arrangement in the greenhouse under high intensity light for a daily photoperiod of 12 hours. Normal watering and fertilizing practices are followed. The plants are harvested three months later, the number of pods, and the fresh and dry weight of same are determined. The data are averaged and are summarized in Table IIa below.

TABLE IIa

The effect of N—isopropyl-2,6-dinitro-4-propyl-m-toluidine on the pod yield of soybeans

| Compound | Rate kg/ha | Pods: Number of/% change | g fresh wt/% change | g dry wt/% change |
| --- | --- | --- | --- | --- |
| Control | — | 102.8 | 120.8 | 31.8 |
| 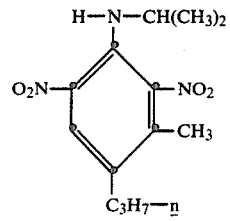 | .00353 | 104.9/2.0 | 116.1/−3.9 | 32.5/2.2 |
|  | .00706 | 114.1/10.9 | 122.9/1.74 | 33.1/4.0 |
|  | .0353 | 114.6/10.9 | 124.5/3.1 | 32.0/— |
|  | .0526 | 114.0/10.9 | 136.2/12.7 | 34.0/7.8 |

The above experiment is repeated excepting that the granular is applied when the germinated plants are at the trifoliate stage, on one side of the plant in a trench 2.5 cm deep and covered.

The plants are harvested three months later, the number of pods, and the fresh and dry weight of pods are determined. The data are averaged and are summarized in Table IIb below.

TABLE IIb

The effect of N—isopropyl-2,6-dinitro-4-propyl-m-toluidine on the pod yield of soybeans

| Compound | Rate kg/ha | Pods: Number of/% change | g fresh wt/% change | g dry wt/% change |
| --- | --- | --- | --- | --- |
| Control | — | 91.7 | 137.1 | 38.6 |
| 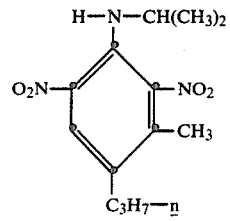 | .00358 | 104.5/13.9 | 141.6/3.3 | 39.8/3.1 |
|  | .00706 | 92.4/.8 | 128.2/−6.5 | 35.0/−9.3 |
|  | .0353 | 108.6/18.4 | 141.1/2.9 | 37.5/−2.8 |
|  | .0526 | 102.1/11.3 | 135.5/−1.2 | 37.9/−1.8 |

EXAMPLE 3

Evaluation of compounds of the invention to increase the branching, and accelerate the blooming of soybeans In the following tests, test compounds are dissolved or dispersed in acetone-water (1:1) mixtures at the final concentration corresponding to the kg/ha rates indicated in the table below. The solution also contains 0.25% v/v colloidal BIOFILM ® (a product of Colloidal Products Corp.) which is a mixture of alkyl aryl polyethoxyethanol, free and combined fatty acids, glycol ethers, dialkylbenzene carboxylate and 2-propanol.

The plant species used in these tests are soybeans (*Glycine max.*) cv. Adelphia.

The solution or dispersion of the compound under test is sprayed at a rate of 747 l/ha with a moving nozzle along an overhead stationary track. The spray nozzle moves at a constant speed over the plants.

The plants are grown in plastic pots, and are well established at the time of treatment. The seedlings of soybeans are at the first trifoliate stage. Plants are watered prior to treatment and then sprayed to provide the kg/ha rate of test compound desired. After spraying the plants are placed on greenhouse benches and watered and fertilized in accordance with normal greenhouse procedures.

Three weeks after treatment the plants are examined to determine what effect the application of test compound had on axillary branching, earlier bloom, and number of flowers of plants.

Increased axillary branching and earlier and increased blooming are biological responses which are highly advantageous in the growing of crops. These responses are frequently indicative of an increase in the production of fruit. Data obtained in these tests are reported in Table III as percent change (increase or decrease) over untreated controls.

TABLE III

Evaluation of the effect of compounds of the invention on the branching, blooming and height of soybeans

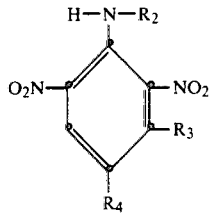

| No. | R2 | R3 | R4 | Rate kg/ha | Branching* | Time of* bloom | Number of* bloom |
|---|---|---|---|---|---|---|---|
| 1 | —H | —CH$_3$ | —CH$_3$ | 0.2 | −10 to −20 | | |
| | | | | 0.4 | +10 to +15 | | |
| | | | | 0.6 | +10 to +15 | | |
| 2 | —H | —CH$_3$ | —SO$_2$NH$_2$ | 0.2 | +20 to +40 | | |
| | | | | 0.4 | +20 to +40 | | |
| | | | | 0.6 | +40 to +60 | | |
| 3 | CH$_3$\|—CH—C$_2$H$_5$ | —OCH$_3$ | —CF$_3$ | 0.2 | +10 to +20 | | |
| | | | | 0.4 | +10 to +20 | | |
| | | | | 0.6 | normal | | |
| 4 | —CH(C$_2$H$_5$)$_2$ | —CH$_2$OCH$_3$ | —C$_2$H$_5$ | 0.2 | −30 to −40 | | |
| | | | | 0.4 | −50 to −60 | | |
| | | | | 0.6 | −70 to −80 | | |
| 5 | —CH$_2$—CH=CH$_2$ | —CH$_2$OCH$_3$ | —C$_2$H$_5$ | 0.2 | +10 to +20 | | |
| | | | | 0.4 | +10 to +15 | +10 to +20 | |
| | | | | 0.6 | +20 to +40 | | |
| 6 | CH$_3$\|—CH—C$_2$H$_5$ | —CH$_2$OCH$_3$ | —C$_2$H$_5$ | 0.2 | −10 to −20 | | |
| | | | | 0.4 | +10 to +15 | | |
| | | | | 0.6 | +10 to +20 | | |
| 7 | CH$_2$Cl\|—CH—C$_2$H$_5$ | —CH$_2$OCH$_3$ | —CH$_3$ | 0.2 | +10 to +20 | | |
| | | | | 0.4 | +10 to +15 | | |
| | | | | 0.6 | normal | | |
| 8 | —CH(C$_2$H$_5$)$_2$ | —CH$_2$OCH$_3$ | —C$_3$H$_7$—n | 0.2 | normal | | |
| | | | | 0.4 | +10 to +15 | | |
| | | | | 0.6 | 0 to −10 | | |
| 9 | —CH(CH$_3$)$_2$ | —CH$_2$OCH$_3$ | —C$_3$H$_7$—n | 0.2 | +10 to +20 | +10 to +20 | |
| | | | | 0.4 | +10 to +20 | +10 to +20 | |
| | | | | 0.6 | normal | — | |
| 10 | —CH(CH$_3$)$_2$ | —CH$_3$ | —C$_3$H$_7$—n | 0.2 | +10 to +20 | +10 to +20 | +10 to +20 |
| | | | | 0.4 | +20 to +35 | +10 to +20 | +20 to +40 |
| | | | | 0.6 | +20 to +40 | +10 to +20 | +20 to +40 |
| 11 | CH$_2$OCH$_3$\|—CH—C$_2$H$_5$ | —CH$_3$ | —C$_3$H$_7$—n | 0.2 | +20 to +40 | +20 to +40 | |
| | | | | 0.4 | +10 to +20 | +10 to +20 | |
| | | | | 0.6 | −10 to −20 | −10 to −20 | |
| 13 | —CH(CH$_3$)$_2$ | —CH$_3$ | —SO$_2$CH$_3$— | 0.2 | +10 to +20 | | |
| | | | | 0.4 | +10 to +15 | | |
| | | | | 0.6 | +10 to +15 | | |
| 14 | R$_1$ = C$_2$H$_5$**<br>R$_2$ = C$_2$H$_5$ | —CH$_3$ | —SO$_2$CH$_3$ | 0.2 | +10 to +15 | | |
| | | | | 0.4 | normal | | |
| | | | | 0.6 | normal | | |

*+ = increase
− = decrease
** = hydrogen (R$_1$ of generic formula) replaced with C$_2$H$_5$

EXAMPLE 4

Field test to evaluate a compound of the invention for increasing the yield of soybeans Procedure Soybeans (*Glycine max.* var. Williams) are planted in rows 0.81 m wide and 107 m long. The compound under test: N-isopropyl-2,6-dinitro-4-propyl-m-toluidine is dissolved or dispersed in acetone-water (50:50) mixtures at the final concentration corresponding to the kg/ha rates indicated in the Tables IVa and IVb below. Additionally, the solutions may also contain from 0.1% to 0.25% v/v colloidal BIOFILM ® (a product of Colloidal Products Corp.) which is a mixture of alkyl aryl polyoxyethanol, free and combined fatty acids, glycol ethers dialkylbenzene carboxylate and 2-propanol.

Plants are sprayed at the first trifoliate stage to provide the kg/ha rates indicated in the tables below.

Two sets of tests are run. In these tests each treatment is replicated six times. The plants are harvested in about 21 weeks posttreatment, the data obtained are averaged and are reported in Tables IVa and IVb below.

TABLE IVa

Evaluation of the effect of N—isopropyl-2,6-dinitro-4-propyl-m-toluidine on soybeans

| Sample | Rate kg/ha | Fresh wt of harvested soybeans; g | Percent difference from control |
|---|---|---|---|
| Control | — | 2750.83 | — |
| Compound | 0.2 | 2782.17 | 1.14 |
| Control | — | 2821.67 | — |
| Compound | 0.4 | 3582.00 | 26.95 |
| Control | — | 2698.00 | — |
| Compound | 0.6 | 2523.00 | −6.49 |

TABLE IVb

Evaluation of the effect of N—isopropyl-2,6-dinitro-4-propyl-m-toluidine on soybeans

| Sample | Rate kg/ha | Fresh wt of harvested soybeans; g | Percent difference from control |
|---|---|---|---|
| Control | — | 2757.50 | — |
| Compound | 0.2 | 2876.17 | 4.30 |
| Control | — | 2735.83 | — |
| Compound | 0.4 | 3521.00 | 28.70 |
| Control | — | 2756.67 | — |
| Compound | 0.6 | 2838.00 | 2.95 |

Tables IVa and IVb clearly show that N-isopropyl-2,6-dinitro-4-propyl-m-toluidine applied at a rate of 0.4 kg/ha increases the yield of soybeans by about 27% to 29%.

EXAMPLE 5

Evaluation of a test compound for increasing the yield of legumes using soybeans (Glycine max var. York) as the plant species By the method of Example 1, N-isopropyl-2,6-dinitro-4-propyl-m-toluidine is evaluated on soybeans (Glycine max. var. York) as a yield enhancing agent.

In these tests, the soybean seedlings are at the first trifoliate stage when treated. Each test is replicated 7 times.

At, or near maturity the pods are harvested and their fresh and dry weight determined. The yields are averaged and are expressed as percent increase over controls. The data are reported in Table V below.

TABLE V

Evaluation of a test compound to increase the yield of soybean pods

| Compound | Rate kg/ha | Pods: Number of/ % change | Fresh wt in g/% change | Dry wt in g/% change |
|---|---|---|---|---|
| Control | — | 84.1 | 46.7 | 8.7 |
| 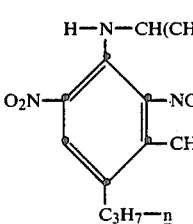 | 0.224 | 92.1/9.5 | 57.1/22.7 | 10.9/25.3 |
|  | 0.448 | 86.4/2.7 | 58.9/26.1 | 10.5/20.7 |
|  | 0.672 | 103.8/23.4 | 62.9/34.7 | 12.3/41.7 |

EXAMPLE 6

Evaluation of the preemergence yield enhancing activity of N-isopropyl-2,6-dinitro-4-propyl-m-toluidine on legumes, using snapbeans (Phaseolus spp) as the plant species Snapbean (Phaseolus spp) seeds are planted in separated cups. After planting the soil surface in the cups is sprayed with the aqueous acetone solution of N-isopropyl-2,6-dinitro-4-propyl-m-toluidine to provide the kg per hectare rates given in Table VI below. The treated cups are then placed on greenhouse benches, watered and cared for in accordance with conventional greenhouse procedures. At or near maturity, the pods are harvested, their number, fresh and dry weight determined. The averaged data are expressed as percent increase over controls. The data are reported in Table VI below.

TABLE VI

Evaluation of the yield enhancing activity of N—isopropyl-2,6-dinitro-4-propyl-m-toluidine on snapbeans

| Compound | Rate kg/ha | Snapbean pods Number of/ % change | Fresh wt in g/% change | Dry wt in g/% change |
|---|---|---|---|---|
| Control | — | 18.9 | 56.2 | 5.0 |

TABLE VI-continued

Evaluation of the yield enhancing activity of N—isopropyl-2,6-dinitro-4-propyl-m-toluidine on snapbeans

| Compound | Rate kg/ha | Snapbean pods Number of/ % change | Fresh wt in g/% change | Dry wt in g/% change |
|---|---|---|---|---|
| H—N—CH(CH$_3$)$_2$ on 2,6-dinitro-4-propyl-m-toluidine (O$_2$N, NO$_2$, CH$_3$, C$_3$H$_7$—n) | 2.24 | 20.1/6.4 | 56.3/0.2 | 5.3/6.0 |
| | 1.12 | 21.5/13.8 | 63.8/13.5 | 5.6/12.0 |
| | 0.56 | 19.5/3.2 | 61.7/9.8 | 5.9/18.0 |
| | 0.28 | 18.5/−2.1 | 63.3/12.6 | 5.5/10.0 |

EXAMPLE 7

Evaluation of the effect of a compound of the invention on the yields of snapbeans (*Phaseolus vulgaris*, var. Sprite) treated at various stages of their growth In the following tests, N-isopropyl-2,6-dinitro-4-propyl-m-toluidine is dissolved in acetone:water (50:50) mixtures at the final concentration corresponding to the kg/ha rates indicated in Table VII below. Each treatment is replicated 8 times.

Snapbean (*Phaseolus vulgaris*, var. Sprite) plants are treated at: the first trifoliate (Stage I) stage, the fifth trifoliate (Stage II) stage, the early bloom (Stage III) stage, and the mid-bloom-part-set (Stage IV) stage.

The pots are watered, treated and placed on benches in a random arrangement in the greenhouse. Normal watering and fertilizing practices are followed (pesticides are applied to the plants as needed). Minimum day and night temperature of 18° C. is maintained during cooler periods of the year. Normal daily fluctuations occur during the summer season. At or near maturity the plants are harvested, the number of pods, and their fresh and dry weight is determined and expressed as percent change (+ =increase; − =decrease) from control. The data are averaged and reported in Table VII below.

TABLE VII

Evaluation of the affect of N—isopropyl-2,6-dinitro-4-propyl-m-toluidine on the yields of snapbeans (*Phaseolus vulgaris*, var. Sprite)

| Compound | Rate kg/ha | Pods: Number of/ % change | Fresh wt in g/% change | Dry wt in g/% change |
|---|---|---|---|---|
| Stage I | | | | |
| Control | — | 17.7 | 60.9 | 6.0 |
| H—N—CH(CH$_3$)$_2$ (O$_2$N, NO$_2$, CH$_3$, C$_3$H$_7$—n) | 0.224 | 17.8/0.6 | 54.1/−11.2 | 5.5/−8.3 |
| | 0.448 | 19.0/7.3 | 57.9/−4.9 | 6.1/1.7 |
| | 0.672 | 19.2/8.5 | 49.7/−18.4 | 4.6/−23.3 |
| Stage II | | | | |
| Control | — | 18.5 | 69.3 | 6.9 |
| H—N—CH(CH$_3$)$_2$ (O$_2$N, NO$_2$, CH$_3$, C$_3$H$_7$—n) | 0.224 | 17.4/−5.9 | 77.7/12.1 | 8.2/18.8 |
| | 0.448 | 18.2/−1.6 | 78.5/13.3 | 8.2/18.8 |
| | 0.672 | 17.5/−5.4 | 78.1/12.7 | 8.3/20.3 |
| Stage III | | | | |
| Control | — | 17.3 | 73.4 | 7.7 |

TABLE VII-continued

Evaluation of the affect of N—isopropyl-2,6-dinitro-4-propyl-m-toluidine on the yields of snapbeans (*Phaseolus vulgaris*, var. Sprite)

| Compound | Rate kg/ha | Pods: Number of/ % change | Fresh wt in g/% change | Dry wt in g/% change |
| --- | --- | --- | --- | --- |
| 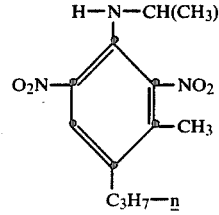 | 0.224 | 16.0/−7.5 | 84.2/14.7 | 9.2/19.5 |
| | 0.448 | 15.7/−9.2 | 71.1/−3.1 | 7.4/−3.9 |
| | 0.672 | 16.7/−3.5 | 79.4/8.2 | 8.2/6.5 |

| | | Stage IV | | |
| --- | --- | --- | --- | --- |
| Control | — | 20.3 | 74.7 | 7.4 |
| 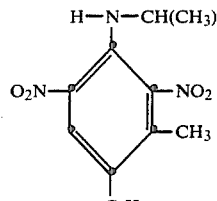 | 0.224 | 16.3/−19.7 | 73.7/−1.3 | 8.2/10.8 |
| | 0.448 | 16.8/−17.2 | 77.4/3.6 | 7.9/6.7 |
| | 0.672 | 18.3/−9.8 | 77.6/3.9 | 8.4/13.5 |

EXAMPLE 8

Field test to evaluate N-isopropyl-2,0-dinitro-4-n-propyl-m-toluidine for increasing the yield of potatoes Potatoes (*Solanum tuberosum* var. superior) are planted 0.30 m apart in rows 0.91 m wide and 11 m long. The compound under test: N-isopropyl-2,6-dinitro-4-n-propyl-m-toluidine is dissolved or dispersed in acetone:-water (50:50) mixtures at the final concentrations indicated in Table VIII below. Additionally the spray solutions also contain 0.25% v/v of spreader: X-77 ® (a product of Ortho Corp.) which is a mixture of alkyl aryl polyoxyethylene glycols, free fatty acids and 2-propanol.

The plants are sprayed at one, two, three and five weeks postemergence at the rates indicated in Table VIII below. In these tests, each treatment is replicated six times using paired controls. The potatoes are harvested in about 14 weeks posttreatment and the yields per test are averaged and from these data the percent change over the control calculated. The results are summarized in Table VIII below.

TABLE VIII

Evaluation of N—isopropyl-2-6-dinitro-4-n-propyl-m-toluidine for increasing the yield of potatoes, applied postemergence

| Compound | Rate kg/ha | Percent change over controls when treated weeks, postemergence* | | | |
| --- | --- | --- | --- | --- | --- |
| | | 1 | 2 | 3 | 5 |
| N—isopropyl-2,6-dinitro-4-n-propyl-m-toluidine | 1.0 | +3.2 | +25.6 | +13.7 | −3.0 |
| | 0.5 | +10.6 | +33.8 | +14.3 | −4.8 |
| | 0.25 | +15.6 | +35.0 | +11.6 | −8.7 |

*= + = increase
− = decrease

EXAMPLE 9

Evaluation of the yield enhancing activity of N-isopropyl-2,6-dinitro-4-n-propyl-m-toluidine, applied postemergence, using sugar beets as the plant species Sugar beets (*Saccharum officinarum* var. Monogram) are planted in separate 12.5 cm diameter fiber pots. The compound under test: N-isopropyl-2,6-dinitro-4-n-propyl-m-toluidine is dissolved or dispersed in water at the final concentrations indicated in Table IX below. The solutions also contain 0.1% to 0.25% v/v colloidal BIOFILM ® (a product of Colloidal Products Corp.) which is a mixture of alkyl aryl polyethoxyethanol, free and combined fatty acids, glycol ethers, dialkylbenzene carboxylate and 2-propanol.

In these tests, the sugar beet seedlings are at the eight leaf stage when treated.

The pots are watered, treated and placed on benches in a random arrangement in the greenhouse. Normal watering and fertilizing practices are followed (pesticides are applied to the plants as needed). Minimum day and night temperature of 18° C. is maintained during cooler periods of the year. Normal daily fluctuations occur during the summer season.

Plants are sprayed to provide a kg/ha rates indicated in Table IX below.

The sugar beets are harvested 70 days posttreatment and dried. The yields are averaged and compared to those obtained from the untreated controls, and are expressed as percent change (±) over the controls.

TABLE IX

Evaluation of N—isopropyl-2,6-dinitro-4-n-propyl-m-toluidine for increasing the yield of sugar beets, applied postemergence at the eight leaf stage

| Compound | Rate kg/ha | Percent change (±)* in yields over controls | | |
|---|---|---|---|---|
| | | Leaf fresh wt | Root fresh wt | Root dry wt |
| Control | — | 0 | 0 | 0 |
| N—isopropyl- | 0.25 | −0.3 | +15.4 | +5.3 |
| 2,6-dinitro- | 0.50 | −1.1 | +29.4 | +17.8 |
| 4-n-propyl- | 0.75 | +2.9 | +25.6 | +14.2 |
| m-toluidine | 1.00 | +10.3 | +17.3 | +1.6 |
| | 1.50 | −18.3 | −22.7 | −33.6 |

\* = + = increase over control
− = decrease over control

We claim:

1. A method to improve the yield of leguminous crops said method comprising applying in a non-phytotoxic amount to the foliage, stems and roots of leguminous plants or to seeds of the plants in soil containing the seeds an effective amount of a compound, for the compound to metabolically stimulate and enhance the yield of plants by altering the growth and development of the plants, said compound being of the formula:

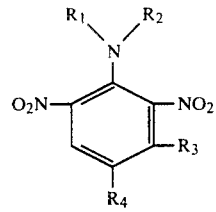

wherein
$R_1$ is H;
$R_2$ is $CH(CH_3)_2$, $CH(CH_3)C_2H_5$, $CH(C_2H_5)_2$ or $$\begin{array}{c} CH-C_2H_5; \\ | \\ CH_2OCH_3 \end{array}$$

$R_3$ is $CH_3$ or $CH_2OCH_3$;
$R_4$ is $C_2H_5$, n-$C_3H_7$, or i-$C_3H_7$.

2. A method according to claim 1, wherein the compound is N-isopropyl-2,6-dinitro-4-propyl-m-toluidine.
3. A method according to claim 1, wherein the compound is N-isopropyl-alpha-methoxy-2,6-dinitro-4-propyl-m-toluidine.
4. A method according to claim 1, wherein the compound is applied in amounts of from 0.1 kg per hectare to 1.0 kg per hectare.
5. A method according to claim 1, wherein the amount is from 0.2 kg to 0.6 kg per hectare.
6. A method according to claim 1 wherein N-isopropyl-2,6-dinitro-4-propyl-m-toluidine is applied in amounts from 0.2 kg to 0.6 kg per hectare.
7. A method according to claim 1, wherein leguminous plants are beans (Phaseolus vulgaris, spp).

* * * * *